United States Patent [19]

Baskent et al.

[11] 4,306,035

[45] Dec. 15, 1981

[54] USE OF ALKOXYSILICON COMPOSITIONS AS FOAM STABILIZERS IN HIGH RESILIENCE POLYURETHANE FOAMS

[75] Inventors: Feyyaz O. Baskent, Mahopac, N.Y.; James D. Reedy, New Fairfield, Conn.

[73] Assignee: Union Carbide Corporation, New York, N.Y.

[21] Appl. No.: 154,849

[22] Filed: May 30, 1980

[51] Int. Cl.$^3$ ..................... C08G 18/14; C08G 18/08; C09K 3/00

[52] U.S. Cl. .................................. 521/110; 252/350; 252/DIG. 1; 556/457; 556/482

[58] Field of Search ................ 521/110; 556/457, 482; 252/350, DIG. 1

[56] References Cited

U.S. PATENT DOCUMENTS

| | | | |
|---|---|---|---|
| 2,415,389 | 2/1947 | Hunter et al. | 260/462 |
| 2,909,549 | 10/1959 | Bailey | 525/477 |
| 2,947,772 | 8/1960 | Eynon et al. | 556/482 |
| 3,050,477 | 8/1962 | Gmitter et al. | 521/110 |
| 3,741,917 | 6/1973 | Morehouse | 521/112 |
| 3,839,384 | 10/1974 | Morehouse | 260/448.2 R |
| 3,905,924 | 9/1975 | Prokai | 521/160 |
| 4,039,490 | 8/1977 | Kanner | 521/110 |
| 4,042,540 | 8/1977 | Lammerting et al. | 521/111 |

FOREIGN PATENT DOCUMENTS 795335 5/1958 United Kingdom ................ 521/110

OTHER PUBLICATIONS

Eaborn—Organosilicon Compounds, Academic Press, N.Y. (1960), pp. 246-250, 277-279, 454-457, and 460-461.

Bazant et al., Organosilicon Compounds, Academic Press, N.Y. (1965), vol. 2, p. 685.

*Primary Examiner*—H. S. Cockeram
*Attorney, Agent, or Firm*—Francis M. Faxio

[57] ABSTRACT

A process for manufacturing low density high resilience polyurethane foams utilizing as a foam stabilizer selected low molecular weight alkoxysilicon compositions containing from one to 18 silicon atoms in which the alkoxy-modifying group contains from 5 to 18 carbon atoms; solutions of such alkoxysilicon compositions; and the foams derived from such process.

36 Claims, No Drawings

USE OF ALKOXYSILICON COMPOSITIONS AS FOAM STABILIZERS IN HIGH RESILIENCE POLYURETHANE FOAMS

RELATED APPLICATION

Baskent, F. O. and Reedy, J. D., Ser. No. 134,637, filed Mar. 27, 1980, for: Alkyl-Modified Siloxane Copolymers Useful As Foam Stabilizers In High Resilience Polyurethane Foam.

FIELD OF THE INVENTION

This invention relates to a process for manufacturing low density high resilience polyurethane foam utilizing selected low molecular weight alkoxysilicon compositions as foam stabilizers.

BACKGROUND OF THE INVENTION

Basically high resilience polyurethane foams are produced by the reaction of highly primary hydroxyl-capped, high molecular weight polyols with organic isocyanates and water. High resilience polyurethane foams are distinguishable, in part, from conventional hot cure polyurethane foams by the use of such polyols and the fact that high resilience polyurethane foams require little or no oven curing and thus are often referred to as cold cure foams. Such foams are extremely desirable for cushioning applications because of their excellent physical properties, e.g., very high foam resilience, low flammability, open-celled structure, low flex fatigue (long life) and high SAC factors (load bearing properties).

Because of the high reactivity of high resilience foam ingredients and their rapid buildup of gel strength, sometimes the foam can be obtained without a cell stabilizer. However such foams typically have very irregular cell structure as particularly evidenced by surface voids and the lack of discovery of a proper agent to help control cell structure has been a major problem in the art.

Attempts to solve this problem with surfactants generally employed in the stabilization of hot cure polyurethane foam have not proven satisfactory because such surfactants tend to overstabilize, causing extremely tight, shrinking foam. Nor is the problem corrected by reducing the concentrations of such surfactants, since at concentrations required to eliminate shrinkage, the cells are no longer stabilized satisfactorily and the foam structure becomes irregular, coarse and contains surface voids.

U.S. Pat. No. 4,042,540 discloses that a variety of low viscosity siloxanes, including low viscosity alkoxymodified siloxanes and low viscosity dimethylsilicone oils, are better stabilizers for high resilience polyurethane foams than higher viscosity dimethylsilicone oils. The alkoxy groups in the low viscosity siloxanes preferably contain from one to six (apparently more preferably one to four) carbon atoms. The low viscosity siloxanes contain from four to twelve silicon atoms and contain only very small amounts of siloxane species containing more than twelve silicon atoms (e.g., less than 0.5% by weight). Such higher molecular weight siloxanes can be removed by fractional distillation. There is no suggestion of any particular benefit resulting from the use of any alkoxysilicon composition wherein the alkoxy groups contain from five to eighteen carbon atoms.

Several other patents disclose the use of organosiloxane copolymers as foam stabilizers in high resilience foam formulation. U.S. Pat. No. 3,905,924 relates to the use of cyanoalkylsiloxane copolymers as stabilizers for high resilience polyurethane foam. U.S. Pat. No. 3,741,917 describes siloxane-oxyalkylene copolymers and the use of said organosiloxane copolymers in the formulation of high resilience polyurethane foam. U.S. Pat. No. 3,935,133 teaches the use of high molecular weight silicate esters of polyether alcohols to stabilize high resilience polyurethane foam. U.S. Pat. Application Ser. No. 932,637, filed Aug. 10, 1978, now U.S. Pat. No 4,210,726 discloses a process for producing high resilience polyurethane foam utilizing as a foam stabilizer a combination of an organosiloxane copolymer and a hydrocarbon oil. However, none of the latter mentioned patents or application disclose alkoxysilicon compositions and their use as foam stabilizers in the manufacture of low density high reslience polyurethane foam.

Several other references disclose alkoxysilicon compositions. Alkoxysilane monomer structures such as dimethyldioctoxysilane are described in a reference text entitled "Organosilicon Compounds" by Vladimir Bazant et al., Academic Press, New York and London, 1965, Vol. 2, page 685. U.S. Pat. Application Ser. No. 579,600, filed May 21, 1975, now U.S. Pat. No. 4,261,848 relates to alkoxysiloxanes characterized by alkoxy end-blocking groups derived from alcohols having boiling points and solidification points in particular ranges, and the use of these alkoxysiloxanes as hydraulic fluids. U.S. Pat. No. 2,909,549 teaches a method for making alkoxy-end-blocked silicone polymers such as trialkoxypolysiloxane polymers, and the use of the alkoxy end-blocked silicone polymers as industrial oils, intermediates, dielectric agents and water-repellent agents. However, none of the latter mentioned references disclose the use of alkoxysilicon compositions as foam stabilizers in the manufacture of low density high resilience polyurethane foam.

Within the past few years, cushions fabricated from high resilience polyurethane foam have gained increasingly wide acceptance in automotive seatings. Automotive industry requirements decreased from the foam density needed for seat cushions, thus increasing the difficulty of stabilization of high resilience polyurethane foam. Recently new polymer/polyol systems with high water levels have been proposed which can produce foam cushions with densities of 1.50 to 1.75 lbs./cubic foot and acceptable physical properties in comparison to the commercial foaming systems. However, without any foam stabilizing surfactant, the new polymer/-polyol-high water systems produced foams with large and irregular cells or caused collapse of the foam. The addition of commercial high resilience polyurethane foam surfactants (including the low viscosity propoxy-modified siloxanes, the low viscosity dimethylsilicone oils, cyanoalkylsiloxane copolymers and siloxane-oxyalkylene copolymers disclosed in the above-mentioned patents) to this new polymer/polyol-high water system did not correct these problems. The commercial high resilience polyurethane foam surfactants caused collapse of the foams, and commercial flexible "hot-cure" polyurethane surfactants caused severe shrinkage and pneumatic foams. Thus, it is a problem in low density high resilience polyurethane foam formulations to obtain a surfactant which has a proper degree of cell stabilizing ability. This problem is solved by the present invention and also by copending U.S. Application Ser.

No. 134,637, filed Mar. 27, 1980, which describes novel alkylmodified siloxane copolymers having beneficial utility as foam stabilizers in the formulation of low density high resilience polyurethane foam.

SUMMARY OF THE INVENTION

This invention is based on the discovery that certain low molecular weight alkoxysilicon compositions can be used to control the cell uniformity of low density high resilience polyurethane foam with little, if any, foam shrinkage. Moreover, voids in the foam are eliminated (or at least greatly reduced) by the instant invention and the cell structure of the low density high resilience polyurethane foam is also much more uniform and finer than where no surfactant agent is used. The present invention provides for the use of three types of low molecular weight alkoxysilicon compositions as foam stabilizers in low density high resilience polyurethane foam formulation in which the alkoxy-modifying group contains from 5 to 18 carbon atoms and the silicon-bearing group contains from 1 to 18 silicon atoms. The use of these alkoxysilicon compositions as foam stabilizers unexpectedly produce low density high resilience polyurethane foams with excellent cell structure in comparison to current high resilience polyurethane foam stabilizers.

The alkoxysilicon compositions are selected from the group consisting of: (a) an alkoxysilane monomer having the average formula,

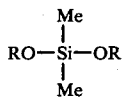　　　(I)

wherein Me is a methyl group and R is an alkyl group having from 6 to 18 carbon atoms inclusive; (b) an alkoxysiloxane copolymer having the average formula,

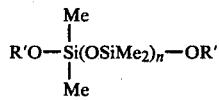　　　(II)

wherein Me is a methyl group, R' is an alkyl group having from 7 to 18 carbon atoms inclusive in which the R' groups represent from 15 to 75 weight percent of the alkoxysiloxane copolymer, and n has an average value from one to 12 inclusive; and (c) an alkoxysiloxane copolymer having the average formula,

　　　(III)

wherein Me is a methyl group, R'' is an alkyl group having from 5 to 18 carbon atoms inclusive in which the R'' groups represent from 15 to 70 weight percent of the alkoxysiloxane copolymer, x has an average value from one to three inclusive, y has an average value from zero to (18-x) inclusive, and z has an average value from 3 to 5 inclusive. Illustrative of the groups represented by R in formula I are hexyl, heptyl, octyl, nonyl, decyl and the like, preferably R has from 6 to 16 carbon atoms inclusive. Illustrative of the groups represented by R' in Formula II are heptyl, octyl, nonyl, decyl, undecyl and the like, preferably R' has from 7 to 14 carbon atoms inclusive. Illustrative of the groups represented by R'' in formula III is pentyl, hexyl, heptyl, octyl, nonyl and the like, preferably R'' has from 5 to 12 carbon atoms inclusive. R, R' and R'' may be either the same or different alkyl group in Formula I, Formula II and Formula III respectively.

More specifically the present invention relates to the use of these alkoxysilicon compositions as cell stabilizers in a process for preparing low density high resilience polyurethane foam having a density of no greater than 2.0 pounds per cubic foot (preferably no greater than 1.75 pounds per cubic foot), said process comprising foaming and reacting a reaction mixture comprising: (a) an organic polyol selected from the group consisting of (i) a polyether triol containing at least 40 mole percent primary hydroxyl groups and having a molecular weight from about 2000 to about 8000 and (ii) a mixture of said polyether triol and other polyethers having an average of at least two hydroxyl groups, said polyether triol of said mixture amounting to at least 40 weight percent of the total polyol content; (b) a polyisocyanate, said organic polyol and said polyisocyanate being present in the mixture in a major amount and in the relative amount required to produce the polyurethane foam; (c) a blowing agent in a minor amount sufficient to foam the reaction mixture; (d) a catalytic amount of catalysts for the production of polyurethane foam; (e) a minor amount of a foam stabilizer comprising an alkoxysilicon composition; and, optionally, (f) a flame retardant in a minor amount sufficient to retard the flammability of the polyurethane foam. Low density high resilience polyurethane foams obtained according to the process of this invention have uniform cell structure and a smooth molding surface. In addition, the alkoxysilicon compositions are operable over a broad range (e.g. 0.02 to 5.0 parts by weight per hundred parts by weight of the polyether polyol) and can be used in solution and consequently are easy to meter and pump during foam formulation.

DESCRIPTION OF PREFERRED EMBODIMENTS

The functionality of the respective types of structural units encompassed by the alkoxysilicon composition of Formula (III) denotes the number of oxygen atoms in which the silicon atom (Si) of any particular unit is bonded. Since each oxygen atom is shared by a silicon (Si) of another unit, functionality also denotes the number of linkages by which the particular unit can be bonded to another portion of the polymer through —Si—O—Si—bonds. Accordingly, in expressing the individual formulas of the respective units encompassed by the alkoxysilicon composition of Formula (III), fractional subscripts are used in which the value of the numerator defines functionality (i.e., the number of oxygen atoms associated with the silicon atom of the particular unit), and the denominator, which in each instance is 2, denotes that each oxygen atom is shared with another silicon atom.

The alkoxysilicon compositions of Formula (I), Formula (II) and Formula (III) can be prepared by several methods. A preferred method involves the preparation of a mixture consisting of a hydrocarbon alcohol having from 5 to 18 carbon atoms and an alkoxy end-blocked silicon fluid selected from the group consisting of:

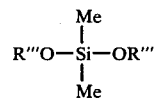　　　(IV)

wherein R''' is an alkyl such as methyl, ethyl, propyl or isopropyl and Me is a methyl group;

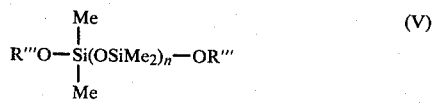 (V)

wherein R''' is an alkyl such as methyl, ethyl, propyl or isopropyl and Me and n are as defined for formula (II) above; and

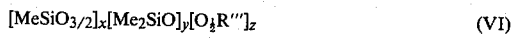 (VI)

wherein R''' is an alkyl such as methyl, ethyl, propyl or isopropyl and Me, x, y, and z are as defined for Formula (III) above. A catalyst is added to the mixture in a preferred concentration of 0.5 weight percent based on the total weight of the alkoxy end-blocked silicon fluid and hydrocarbon alcohol reactants, although higher and lower concentrations of catalyst may be used. A preferred catalyst for this reaction is trfluoroacetic acid. A solvent is also added to the mixture in a preferred concentration of 50 weight percent based on the total weight of the alkoxy end-blocked silicon fluid and hydrocarbon alcohol reactants, although higher and lower concentrations of solvent may be used. Those solvents which are reactive with the Si—OR''' group of the alkoxy endblocked silicon fluid should not be employed in the reaction mixture. Methanol, ethanol, propanol and ether alcohols are in this class. Hydrocarbon solvents such as benzene, toluene and xylene are useful solvents for the reaction. Ethers are another useful class of solvents. The preferred solvent for this reaction is toluene. This mixture is heated to reflux in a 500 ml reaction flask equipped with a mechanical stirrer, thermomenter, distillation column with head and a collecting flask. A low molecular weight alcohol such as methanol, ethanol, propanol or isopropanol is formed as a by-product of the reaction by transesterification. The low molecular weight alcohol by-product is removed from the reaction mixture as an alcohol-solvent azeotrope upon heating the reaction mixture to reflux. After the transesterification reaction is complete, the remaining solvent is removed from the reaction flask by distillation. Usually sodium bicarbonate (NaHCO$_3$) is added to the reaction mixture to effect neutralization, and the resultant product is then pressure filtered. The product so produced is an alkoxy-silicon composition represented by Formula (I), Formula (II) or Formula (III) above.

The relative amount of alkoxysilicon composition used to make the polyurethane foam can vary over wide ranges and are generally employed in amounts ranging from about 0.02 to about 5 parts by weight or greater per hundred parts by weight of the organic polyol starting material. Generally there is no commensurate advantage to using amounts of the alkoxysilicon composition greater than about five parts by weight, while the use of amounts below 0.02 parts by weight can result in foam instability. Preferably the alkoxysilicon compositions are employed in amounts ranging from 0.2 to about 2.0 parts by weight per hundred parts by weight of the organic polyol starting material.

The polyhydroxyl reactants (organic polyols) employed in this invention as the starting materials to prepare the polyurethane foams can be any polyether triol containing at least 40 mole percent of primary hydroxyl groups and having a molecular weight from about 2,000 to about 8,000. Conversely said polyether triols can contain no more than 60 mole percent of secondary hydroxyl groups. Preferably said polyether triols contain about 55 to 90 mole percent of primary hydroxyl groups and have a molecular weight from about 4,000 to about 7,000. The preferred polyether triols used in this invention are polyalkylene-ether triols obtained by the chemical addition of alkylene oxides to trihydroxyl organic containing materials, such as glycerol; 1,2,6-hexanetriol; 1,1,1-trimethylolethane; 1,1,1-trimethylolpropane; and the like, as well as mixtures thereof. The alkylene oxides employed in producing the preferred polyethers described above normally have from 2 to 4 carbon atoms, inclusive while propylene oxide and mixtures of propylene oxide and ethylene oxide are especially preferred.

The organic polyol starting materials used in this invention can be mixtures consisting essentially of said above defined polyether triols and other polyether polyols having an average of at least two hydroxyl groups, said above defined polyether triols amounting to at least 40, preferably at least 50, weight percent of the total polyol content of the mixtures. Illustrative of such other polyethers are triols outside of the scope defined above, diols, tetraols and polymer/polyols, and the like, as well as mixtures thereof. Examples of such polyether polyols that can be mixed with the above defined polyether triols include those adducts of alkylene oxide to such polyols as diethylene glycol; dipropylene glycol; pentaerythritol; sorbitol; sucrose; lactose; alphamethylglucoside; alpha-hydroxyalkyglucoside; novolac resins; water; ethylene glycol; propylene glycol; trimethylene glycol; 1,2-butylene glycol; 1,3-butanediol; 1,4-butanediol; 1,5-pentanediol; 1,2-hexane glycol; 1,10-decanediol; 1,2-cyclohexanediol; 2-butene-1,4-diol; 3-cyclohexane-1,1-dimethanol; 4-methyl-3-cyclohexene-1,1-dimethanol; 3-methylene-1,5-pentanediol; 4-(2-hydroxyethoxy)-1-butanol; and the like; as well as mixtures thereof.

Another type of polyether polyol that can be mixed with the above defined polyether triols and used as the starting materials in this invention are graft polymer/polyether compositions obtained by polymerizing ethylenically unsaturated monomers in a polyether as described in British Pat. No. 1,063,222 and U.S. Pat. No. 3,383,351. Suitable monomers for producing such compositions include, for example, acrylonitrile, vinyl chloride, styrene, butadiene, vinylidene chloride, and the like. Suitable polymers for producing such compositions include, for example, those polyethers hereinabove-described. These graft copolymer/polyether compositions can contain from about 1 to about 70 weight percent, preferably about 5 to about 50 weight percent and most preferably about 10 to about 40 weight percent of the unsaturated monomer polymerized in the polyether. Such compositions are conveniently prepared by polymerizing the monomer in the selected polyether at a temperature of 40° to 150° C. in the presence of a free radical polymerization catalyst, such as peroxides, persulfates, percarbonates, perborate and azo compounds as more fully described by the above patent references. The resulting compositions may contain a small amount of unreacted polyether, monomer and free polymer as well as the graft polymer/polyether complex. Especially preferred are the graft polymer/polyethers obtained from mixtures of acrylonitrile and styrene and polyether triols.

The particular organic polyol or polyols employed as the starting materials of this invention merely depend on the end use of the cold cure polyether urethane foam. For instance, the employment of polyether triols having at least 40 mole percent primary hydroxyl groups and molecular weights from 2,000 to 8,000 preferably 4,000 to 7,000 generally have hydroxyl numbers from 84 to 20, preferably 42 to 20 and give primarily flexible polyether foams. The supplementary polyethers which may have any proportion of primary to secondary hydroxyl groups and which may be mixed with the required polyether triols can be used to control the degree of softness of the foam or vary the load bearing properties of the foam. Such limits are not intended to be restrictive, but are merely illustrative of the large number of possible combinations of polyether triols and other polyethers that can be employed.

The hydroxyl number is defined as the number of milligrams of potassium hydroxide required for the complete neutralization of the hydrolysis product of the fully acetylated derivative prepared from one gram of polyol or mixtures of polyols with or without other crosslinking additives used in the invention. The hydroxyl number can also be defined by the equation:

$$OH = (56.1 \times 1000 \times f)/M.W.$$

wherein OH is the hydroxyl number of the polyol, f is its functionality and m.w. is its molecular weight.

A variety of organic isocyanates can be employed in the foam formulations of this invention for reaction with the organic polyol starting materials above described to provide cold cure polyether urethane foams. Preferred isocyanates are polyisocyanates and polyisothiocyanates of the general formula:

$$Q(NCY)_i$$

wherein Y is oxygen, i is an integer of two or more and Q is an organic radical having the valence of i. For instance, Q can be a substituted or unsubstituted hydrocarbon radical, such as alkylene and arylene, having one or more aryl-NCY bonds and/or one or more alkyl-NCY bonds. Q can also include radicals such as —Q-ZO—, where Q is an alkylene or arylene group and Z is a divalent moiety such as CO, $SO_2$ and the like. Examples of such compounds include hexamethyl diisocyanate, 1,8-diisocyanato-p-methane, xylylene diisocyanates, $(OCNCH_2CH_2CH_2OCH_2)_2O$, 1-methyl-2,4-diisocyanatocyclohexane, phenylene diisocyanates, tolylene diisocyanates, chlorophenylene diisocyanates, diphenylmethane-4,4'-diisocyanate, naphthlene-1,5-diisocyanate, triphenylmethane-4,4'-4''-triisocyanate, and isopropylbenzene-alpha-4-diisocyanate. Further included among the isocyanates useful in this invention are dimers and trimers of isocyanates and diisocyanates and polymeric diisocyanates such as those having the general formula:

$$Q(NCY)_i \text{ and } [Q(NCY)_i]_j$$

in which i and j are integers of two or more, and/or (as additional components in the reaction mixtures) compounds of the general formula:

$$L(NCO)_i$$

in which i is one or more and L is a monofunctional or polyfunctional atom or radical. More specifically, the polyisocyanate component employed in the polyurethane foams of this invention also include the following specific compounds as well as mixtures of two or more of them: 2,4-tolylene diisocyanate, 2,6-tolylene diisocyanate, crude tolylene diisocyanate, bis(4-isocyanatophenyl)methane, polymethylene polyphenylisocyanates that are produced by phosgenation of anilineformaldehyde condensation products, 2,4,6-toluenetriisocyanate, and many other organic polyisocyanates that are known in the art, such as those that are disclosed in an article by Siefken, Ann., 565, 75 (1949). In general, the aromatic polyisocyanates are preferred.

Particularly useful isocyanate components of high resilience cold cure formulations within the scope of this invention are combinations of isomeric tolylene diisocyanates and polymeric isocyanates having units of the formula

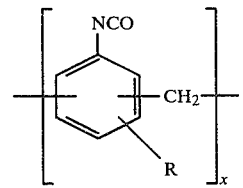

wherein R is hydrogen and/or lower alkyl and x has a value of at least 2.1. Preferably the lower alkyl radical is methyl and x has a value of from 2.1 to about 3.0.

The amount of polyisocyanate employed will vary slightly depending on the nature of the polyurethane being prepared. In general the polyisocyanates are employed in the foam formulations of this invention in amounts that provide from 80 to 150 percent, preferably from 90 to 110 percent of the stoichiometric amount of the isocyanato groups required to react with all of the hydroxyl groups of the organic polyol starting materials and with any water present as a blowing agent. Most preferably, a slight amount of isocyanato groups in excess to the stoichiometric amount is employed.

The blowing agents which can be employed in the process of this invention include water, liquefied gases which have boiling points below 80° F. and above −60° F., or other inert gases such as nitrogen, carbon dioxide, helium and argon. Suitable liquefied gases include saturated aliphatic fluorohydrocarbons which vaporize at or below the temperature of the foaming mass. Such gases are at least partially fluorinated and can also be otherwise halogenated. Fluorocarbon blowing agents suitable for use in foaming the formulations of this invention include trichlorofluoromethane, dichlorodifluoromethane, dichlorofluoromethane, 1,1-chloro-1-fluoroethane, 1-chloro-1,1-difluoro, 2,2-dichloroethane, and 1,1,1-trifluoro-2-chloro-2-fluoro-3,3-difluoro-4,4,4-trifluorobutane. The preferred blowing agent for the process of this invention is trichlorofluoromethane. The amount of blowing agent used will vary the density desired in the foamed product. Usually from 2 to 20 parts by weight of the blowing agent per 100 parts by weight of the organic polyol starting materials are preferred.

The catalysts employed in this invention to produce polyurethanes include any of the amines or metal catalysts used in producing conventional flexible and high resilience polyurethane foam. Illustrative of such conventional amine catalysts are N-methyl morpholine, N-ethyl morpholine, hexadecyl dimethylamine, triethylamine, N,N,N',N'-tetramethyl-1,3-butanediamine, N,N-dimethylethanolamine, diethanolamine, 3-dimethylamino-N,N-dimethylpropionamide, bis(2-dimethylaminoethyl)ether, N,N,N',N'-tetramethyl ethylenediamine, 4,4'-methylene bis(2-chloroaniline), dimethyl benzylamine, N-coco morpholine, triethylene diamine, [1,4-dizabicyclo(2,2,2)-octane], the formate salts of triethylamine diamine, other salts of triethylene diamine and oxyalkylene adducts of primary and secondary amino groups, and the like. Illustrative of such conventional metal catalysts are the tin salts of various carboxylic acids and nickel acetylacetonates. The preferred metal catalyst for the process of this invention is dibutyltindilaurate. Such amine and metal catalysts are preferably employed in the mixtures in an amount from 0.1 to 2 weight percent based on the total weight of the organic polyol starting material.

Other additional ingredients can be employed in minor amounts in producing the high resilience polyurethane foams in accordance with the process of this invention, if desired, for specific purposes. Thus, flame retardants (e.g. trichloroethylphosphite) can be used to reduce any tendency of the polyurethane foam to flammability. Of course any suitable organic solvent for the catalysts can be used which does not substantially adversely affect the operation of the process or reactants. Examples of such solvents for the catalysts include polyols (e.g. 2-methyl-2,4-pentanediol), dipropylene glycol and the like.

In accordance with this invention, the high resilience polyurethane foams can be produced by any suitable technique. The preferred process is a one-step or one shot technique wherein all of the reactants are reacted simultaneously with the foaming operation. A second general process is called the prepolymer process whereby a prepolymer is formed by reacting the polyether starting material with a small excess of the isocyanate and later foaming the prepolymer by the reaction with water or an inert blowing agent. Another method which can be used is the quasi-prepolymer technique which involves reacting a large excess of the isocyanate with the polyether product with additional polyether in the presence of a blowing agent. Sometimes it is preferred to premix the polyether starting material and alkoxysilicon composition although any suitable premixture of the various ingredients can be used. Because of the high exothermic nature of the reaction high resilience polyurethane foams are rapidly produced without the need of any external heat by mixing the reactants at ambient temperatures and pouring the foaming reaction mixture into a suitable mold and allowing the foam to cure itself. Of course, if desired the overall reaction can be even further accelerated by preheating the mold and/or employing conventional high temperature post curing procedures. Within a shorter period of time the cold cure process, with or without post cure, simultaneously achieves a greater degree of cure throughout the entire foam, and shorter tack free and demolding time than is generally achieved with conventional hot cure processes. For instance, high resilience polyurethane foams produced by the cold cure process can be removed from the mold far sooner without substantial damage to the surface than conventional hot cure polyurethane foams. Of course it is to be understood that the cold cure polyurethane foams of this invention can also be prepared in slabstock form, if desired.

An additional feature of the instant invention are the novel compositions suitable for use in producing the high resilience polyether urethane foam. For example it may be desirable, particularly on a commercial scale to employ the alkoxysilicon composition in a diluted form, i.e. in the form of an alkoxysilicon composition-solvent solution premix or an alkoxysilicon composition-solvent catalyst solution premix. Such solution premixes can help serve to eliminate any mixing, metering, or settling problems. Moreover, fewer streams of ingredients may be needed at the mixing head of the operational apparatus. Of considerable importance is that of the formulator has the latitude to select the particular solvent which best suits the system and minimize or eliminate any loss of foam properties. Alkoxysilicon composition-solvent-catalyst premixes can also be used since the selected solvent can be one which serves the dual role of solvent for the catalysts as well as the alkoxysilicon composition. This operation of formulating a premix simplifies the foaming operation and improves the precision of metering ingredients. While any suitable organic solvent such as hydrocarbon, halohydrocarbons, organic hydroxyl compounds, alkyl phthalates, and the like may be employed, preferably when employed the solvent selected should be one in which the alkoxysilicon composition is substantially soluble. For example, it is preferred that at least five parts by weight of the organosiloxane copolymer be soluble in 95 parts by weight of solvent. More preferably the minimum percentage of alkoxysilicon composition in the alkoxysilicon composition-solvent or alkoxysilicon composition-solvent-catalyst solutions should be in the range of at least about ten to at least about 30 weight percent. Of course it is understood that such solvents need not be employed and that the maximum percentage of alkoxysilicon composition in said solvent solutions is not critical. Moreover, when employed such solvent solutions should of course be correlated to the amounts of active alkoxysilicon composition that may be employed per hundred parts by weight of the organic polyol starting material as outlined above. The same correlation should also be made with regard to catalyst when an alkoxysilicon composition -solvent-catalyst solution is employed. Preferably the solvent for the alkoxysilicon composition is an organic hydroxyl compound such as hydroxyl terminated organic ether compounds. More preferably they are polyether triols, diols, and mono-ols such as the adducts of ethylene oxide, propylene oxide, butylene oxide, with starters such as glycerol, water, trimethylolpropane, 1,2,6-hexanetriol, ethylene glycol, butanol, nonylphenol, and the like. Of course the oxyalkylene units of such adducts may be of different types, e.g. oxypropylene and oxyethylene groups, and may be randomly distributed or in blocks. The most preferred solvents are the polyether triols having all or predominantly oxypropylene units in the oxyalkylene portion and having molecular weights in the range from about 2,000 to 6,000 inasmuch as they may be the same as or similar to the primary triols employed as the organic polyol starting material of the foam formulation. Moreover, this discovery concerning the solubility of the alkoxysilicon compositions of this invention can be regulated and controlled.

The high resilience polyurethane foams produced in accordance with this invention can be used for the same purposes as corresponding conventional foams, e.g. they can be used wherever cushioning is desired, e.g. in furniture; in transportation systems, automobiles, planes, etc.; in carpeting; in the packaging of delicate objects; and the like.

The following examples are merely illustrative of the present invention and are not intended as a limitation upon the scope thereof.

ABBREVIATIONS

In the examples, the following abbreviations are used:

| | |
|---|---|
| in. | inch |
| lb. | pound |
| RPM | revolutions per minute |
| PHPP | parts per hundred parts polyol on a weight basis |
| °C. | degree centigrade |
| ml | milliliter |
| cstk | centistroke |
| cc | cubic centimeter |
| min. | minute |
| ft. | feet |
| sec. | seconds |
| percent | weight percent |
| VAZO | Azobisisobutyronitrile |

STARTING MATERIALS

In the following examples, the starting materials described below were used:

a. Polyols

Polyol I

A polyether polyol produced by polymerizing propylene oxide and then ethylene oxide using glycerol as a starter. This polyether polyol has an approximate molecular weight of 4500 and a hydroxyl number of approximately 34. It contains about 85.5 percent by weight propylene oxide, 14.5 percent by weight ethylene oxide and about 73 percent primary hydroxyl groups.

Polyol II

A polyether polyol produced by polymerizing propylene oxide and then ethylene oxide using glycerol as a starter. This polyether polyol has an approximate molecular weight of 4500 and a hydroxyl number of approximately 34. It contains about 85.5 percent by weight propylene oxide, 14.5 percent by weight ethylene oxide and about 80 percent primary hydroxyl groups.

Polymer/Polyol I

A polymer/polyol prepared by polymerizing styrene/acrylonitrile in Polyol I using VAZO as a catalyst. This polymer/polyol has a hydroxyl number of approximately 28. The polymer contains a one to one weight ratio of styrene to acrylonitrile and comprises 21 percent by weight of the total weight of the polymer/polyol.

b. Isocyanates

Isocyanate I

This is a mixture of about 80 weight percent 2,4-tolylene diisocyanate and about 20 weight percent 2,6-tolylene diisocyanate.

Isocyanate II

This is a composition consisting of about 80 weight percent Isocyanate I and about 20 weight percent of a polymethylene polyphenylene isocyanate polymer containing about 2.5 to 2.9 moles of NCO per mole of polymer and having an isocyanate content of about 31.4 percent by weight.

c. Polyurethane Foam Catalysts

Catalyst I

This is a composition consisting of about 70 percent by weight bis-(N,N-dimethylaminoethyl)-ether and about 30 percent by weight dipropylene glycol solvent.

Catalyst II

Bis-(N,N-dimethylaminoethyl)-ether.

Catalyst III

This is a composition consisting of about 33 percent by weight triethylenediamine and about 67 percent by weight dipropylene glycol solvent.

Catalyst IV

This is a composition consisting of about 33.3 percent by weight 3-dimethylamino-N,N-dimethyl-propionamide and 66.6 percent by weight ethoxylated phenol solvent.

Catalyst V

This is a composition consisting of about 88 percent by weight dibutyltindilaurate and about 12 percent by weight polyoxypropylene triol having a molecular weight of about 3000 and a hydroxyl number of about 56.

Catalyst VI

Diethanolamine.

d. Alkoxysilicon Composition Surfactants

Alkoxysilicon Composition Surfactants and Organosiloxane Copolymer Surfactants are described in Examples I through XXXII below.

e. Blowing Agent

Blowing Agent I

Trichlorofluoromethane.

f. Flame Retardant

Flame Retardant I

Trichloroethylphosphite.

EXAMPLE I

PREPARATION OF ALKOXYSILANE MONOMER

Into a 500 ml three-necked reaction flask equipped with a mechanical stirrer, thermometer, distillation column with head, and collecting flask was added 51.8 grams (0.35 mole) of distilled dimethyl diethoxysilane and 82.6 grams (0.70 mole) of 1-octanol. To the reaction flask was also a added a catalyst consisting of 0.5 weight percent trifluoroacetic acid and a solvent consisting of 50 weight percent toluene. The reaction mixture was heated to reflux at atmospheric pressure and a by-product ethanol was formed by transesterification. An ethanol-toluene azeotrope was removed from the reaction mixture upon heating the reaction mixture to reflux. When ethanol formation in the reaction flask had ceased, the remaining toluene was removed by distillation. The product so produced was neutralized with sodium bicarbonate (NaHCO$_3$) and filtered through a pressure filter containing an average filter size of 0.10 microns. The product is an alkoxysilane monomer having a viscosity of 5.9 cstk at a temperature of 25° C. The alkoxysilane monomer is a clear liquid with a calculated molecular weight of 316. The alkoxysilane monomer has the composition,

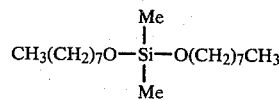

and is hereinafter referred to as Alkoxysilane Monomer A. The composition and properties of Alkoxysilane Monomer A and Alkoxysilane Monomers B and C described hereinafter are tabulated in Table I below.

EXAMPLE II
PREPARATION OF ALKOXYSILANE MONOMER

Into a 500 ml three-necked reaction flask equipped with a mechanical stirrer, thermometer, distillation column with head, and collecting flask was added 51.8 grams (0.35 mole) of distilled dimethyl diethoxysilane and 119.7 grams (0.70 mole) of 1-undecanol. To the reaction flask was also added a catalyst consisting of 0.5 weight percent trifluoroacetic acid and a solvent consisting of 50 weight percent toluene. The reaction mixture was heated to reflux at atmospheric pressure and a by-product ethanol was formed by transesterification. An ethanol-toluene azeotrope was removed from the reaction mixture upon heating the reaction mixture to reflux. When ethanol formation in the reaction flask had ceased, the remaining toluene was removed by distillation. The product so produced was neutralized with sodium bicarbonate (NaHCO$_3$) and filtered through a pressure filter containing an average filter size of 0.10 microns. The product is an alkoxysilane monomer having a viscosity of 14.8 cstk at a temperature of 25° C. The alkoxysilane monomer is a clear liquid with a calculated molecular weight of 403. The alkoxysilane monomer has the composition,

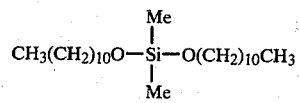

and is hereinafter referred to as Alkoxysilane Monomer B.

EXAMPLE III
PREPARATION OF ALKOXYSILANE MONOMER

Into a 500 ml three-necked reaction flask equipped with a mechanical stirrer, thermometer, distillation column with head, and collecting flask was added 37.0 grams (0.25 mole) of distilled dimethyl diethoxysilane and 120.5 grams (0.50 mole) of 1-hexadecanol. To the reaction flask was also added a catalyst consisting of 0.5 weight percent trifluoroacetic acid and a solvent consisting of 50 weight percent toluene. The reaction mixture was heated to reflux at atmospheric pressure and a by-product ethanol was formed by transesterification. An ethanol-toluene azeotrope was removed from the reaction mixture upon heating the reaction mixture to reflux. When ethanol formation in the reaction flask had ceased, the remaining toluene was removed by distillation. The product so produced was neutralized with sodium bicarbonate (NaHCO$_3$) and filtered through a pressure filter containing an average filter size of 0.10 microns. The product is an alkoxysilane monomer having a viscosity of 21.17 cstk at a temperature of 25° C. The alkoxysilane monomer is a clear liquid with a calculated molecular weight of 543. The alkoxysilane monomer has the composition,

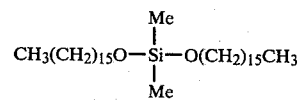

and is hereinafter referred to as Alkoxysilane Monomer C.

EXAMPLE IV
PART A: PREPARATION OF ETHOXY END-BLOCKED SILOXANE FLUID

Into a 500 ml three-necked reaction flask equipped with a mechanical stirrer was added a mixture comprised of 22.2 grams (0.15 mole) of dimethyl diethoxysilane [Me$_2$Si(OCH$_2$CH$_3$)$_2$] and 22.2 grams (0.075 mole) of cyclic dimethylsiloxane tetramer (Me$_2$SiO)$_4$. Also added to the reaction flask was a potassium hydroxide catalyst in an amount corresponding to about one weight percent of the total weight of the mixture. The mixture was heated to a temperature of 130° C. and stirred for about four hours resulting in an equilibrated liquid product. The equilibrated liquid product was neutralized with acetic acid and then filtered through a pressure filter containing an average filter size of about 0.02 microns. The equilibrated liquid product, now properly designated an ethoxy end-blocked siloxane fluid, is a clear liquid with a viscosity of 1.64 cstk at a temperature of 25° C. The dimethylsiloxy (OSiMe$_2$) content of the ethoxy end-blocked siloxane fluid as determined by vapor phase chromatography (VPC) is as follows:

| (OSiMe$_2$)$_a$ Content | Weight Percent in Fluid Mixture |
|---|---|
| a = 1 | 14.3 |
| a = 2 | 14.8 |
| a = 3 | 14.1 |
| a = 4 | 11.9 |
| a = 5 | 9.7 |
| a = 6 | 7.6 |
| a = 7 | 6.0 |
| a = 8 | 4.5 |
| a = 9 | 3.5 |
| a = 10 | 2.6 |
| a = 11 | 2.0 |
| a = 12 | 1.4 |
| a = 13 | 1.1 |
| a = 14 | 0.7 |
| a = 15 | 0.6 |
| a = 16 | 0.4 |
| a = 17 | 0.3 | the vapor phase chromatographic analysis shows 6.5 percent by weight of the ethoxy end-blocked siloxane fluid is comprised of individual dimethysiloxy (OSiMe$_2$) units possessing a value of a > 10. The ethoxy content of the ethoxy end-blocked siloxane fluid is 29.2 percent by weight and the calculated molecular weight is 296. The ethoxy end-blocked siloxane fluid, hereinafter referred to as Ethoxy End-Blocked Siloxane Fluid I, has the average composition:

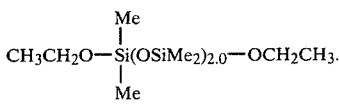

The composition and properties of Ethoxy End-Blocked Siloxane Fluid I and Ethoxy End-Blocked Siloxane Fluids II through V described hereinafter are tabulated in Table II below.

PART B: PREPARATION OF ALKOXYSILOXANE COPOLYMER

Into a 500 ml three-necked reaction flask equipped with a mechanical stirrer, thermometer, distillation column with head, and collecting flask was added 103.6 grams (0.35 mole) of Ethoxy End-Blocked Siloxane Fluid I and 91.0 grams (0.70 mole) of 1-octanol. To the reaction flask was also added a catalyst consisting of 0.5 weight percent trifluoroacetic acid and a solvent consisting of 50 weight percent toluene. The reaction mixture was heated to reflux at atmospheric pressure and a by-product ethanol was formed by transesterification. An ethanol-toluene azeotrope was removed from the reaction mixture upon heating the reaction mixture to reflux. When ethanol formation in the reaction flask had ceased, the remaining toluene was then removed by distillation. The product so produced was neutralized with sodium bicarbonate (NaHCO$_3$) and filtered through a pressure filter containing an average filter size of 0.10 microns. The product is an alkoxysiloxane copolymer having a viscosity of 4.82 cstk at a temperature of 25° C. The dimethylsiloxy (OSiMe$_2$) content of the alkoxysiloxane copolymer as determined by vapor phase chromatography (VPC) is as follows:

| (OSiMe$_2$)$_a$ Content | Weight Percent in Copolymer Mixture |
|---|---|
| a = 1 | 20.4 |
| a = 2 | 16.1 |
| a = 3 | 13.2 |
| a = 4 | 10.3 |
| a = 5 | 6.5 |
| a = 6 | 5.0 |
| a = 7 | 4.3 |
| a = 8 | 2.7 |
| a = 10 | 1.9 |
| a = 11 | 1.7 |
| a = 12 | 1.0 |
| a = 13 | 0.8 |
| a = 14 | 0.6 |

The vapor phase chromatographic analysis shows 4.1 percent by weight of the alkoxysiloxane copolymer is comprised of individual dimethylsiloxy (OSiMe$_2$) units possessing a value of a >10. The alkoxysiloxane copolymer is a clear liquid with a calculated molecular weight of 466. The alkoxysilane copolymer, hereinafter referred to as Alkoxysiloxane Copolymer D, has the average composition,

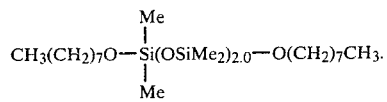

The composition and properties of Alkoxysiloxane Copolymer D and Alkoxysiloxane Copolymers E through H described hereinafter are tabulated in Table III below.

EXAMPLE V

PART A: PREPARATION OF ETHOXY END-BLOCKED SILOXANE FLUID

Into a 500 ml three-necked reaction flask equipped with a mechanical stirrer was added a mixture comprised of 37.0 grams (0.25 mole) of dimethyl diethoxysilane [Me$_2$Si(OCH$_2$CH$_3$)$_2$] and 55.5 grams (0.19 mole) of cyclic dimethylsiloxane tetramer (Me$_2$SiO)$_4$. Also added to the reaction flask was a potassium hydroxide catalyst in an amount corresponding to about one weight percent of the total weight of the mixture. The mixture was heated to a temperature of 130° C. and stirred for about four hours resulting in an equilibrated liquid product. The equilibrated liquid product was neutralized with acetic acid and then filtered through a pressure filter containing an average filter size of about 0.02 microns. The equilibrated liquid product, now properly designated an ethoxy end-blocked siloxane fluid, is a clear liquid with a viscosity of 2.54 cstk at a temperature of 25° C. The ethoxy content of the ethoxy end-blocked siloxane fluid is 24.0 percent by weight and the calculated molecular weight is 370. The ethoxy end-blocked siloxane fluid has the average composition.

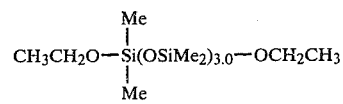

and is hereinafter referred to as Ethoxy End-Blocked Siloxane Fluid II.

PART B: PREPARATION OF ALKOXYSILOXANE COPOLYMER

Into a 500 ml three-necked reaction flask equipped with a mechanical stirrer, thermometer, distillation column with head, and collecting flask was added. 148.0 grams (0.40 mole) of Ethoxy End-Blocked Siloxane Fluid II and 80.8 grams (0.79 mole) of 1-hexanol. To the reaction flask was also added a catalyst consisting of 0.5 weight percent trifluoroacetic acid and a solvent consisting of 50 weight percent toluene. The reaction mixture was heated to reflux at atmospheric pressure and a by-product ethanol was formed by transesterifiction. An ethanol-toluene azeotrope was removed from the reaction mixture upon heating the reaction mixture to reflux. When ethanol formation in the reaction flask had ceased, the remaining toluene was then removed by distillation. The product so produced was neutralized with sodium bicarbonate (NaHCO$_3$) and filtered through a pressure filter containing an average filter size of 0.10 microns. The product is an alkoxysilane copolymer having a viscosity of 5.12 cstk at a temperature of 25° C. The alkoxysiloxane copolymer is a clear liquid with a calculated molecular weight of 482. The alkoxysiloxane copolymer has the average composition,

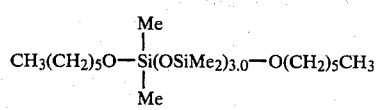

and is hereinafter referred to as Alkoxysiloxane Copolymer E.

EXAMPLE VI

PART A: PREPARATION OF ETHOXY END-BLOCKED SILOXANE FLUID

Into a 500 ml three-necked reaction flask equipped with a mechanical stirrer was added a mixture comprised of 29.6 grams (0.20 mole) of dimethyl diethoxysilane [$Me_2Si(OCH_2CH_3)_2$] and 70.4 grams (0.24 mole) of cyclic dimethylsiloxane tetramer ($Me_2SiO)_4$. Also added to the reaction flask was a potassium hydroxide catalyst in an amount corresponding to about one weight percent of the total weight of the mixture. The mixture was heated to a temperature of 130° C. and stirred for about four hours resulting in an equilibrated liquid product. The equilibrated liquid product was neutralized with acetic acid and then filtered through a pressure filter containing an average filter size of about 0.02 microns. The equilibrated liquid product, now properly designated an ethoxy end-blocked siloxane fluid, is a clear liquid with a viscosity of 3.83 cstk at a temperature of 25° C. The ethoxy content of the ethoxy end-blocked siloxane fluid is 17.1 percent by weight and the calculated molecular weight is 500. The ethoxy end-blocked siloxane fluid has the average composition,

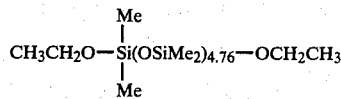

and is hereinafter referred to as Ethoxy End-Blocked Siloxane Fluid III.

PART B: PREPARATION OF ALKOXYSILOXANE COPOLYMER

Into a 500 ml three-necked reaction flask equipped with a mechanical stirrer, thermometer, distillation column with head, and collecting flask was added 150.0 grams (0.30 mole) of Ethoxy End-Blocked Siloxane Fluid III and 78.0 grams (0.60 mole) of 2-ethyl hexanol. To the reaction flask was also added a catalyst consisting of 0.5 weight percent trifluoroacetic acid and a solvent consisting of 50 weight percent toluene. The reaction mixture was heated to reflux at atmosphereic pressure and a by-product ethanol was formed by transesterification. An ethanol-toluene azeotrope was removed from the reaction mixture upon heating the reaction mixture to reflux. When ethanol formation in the reaction flask had ceased, the remaining toluene was then removed by distillation. The product so produced was neutralized with sodium bicarbonate ($NaHCO_3$) and filtered through a pressure filter containing an average filter size of 0.10 microns. The product is an alkoxysiloxane copolymer having a viscosity of 6.34 cstk at a temperature of 25° C. The dimethylsiloxy ($OSiMe_2$) content of the alkoxysiloxane copolymer as determined by vapor phase chromatography (VPC) is as follows:

| $(OSiMe_2)_a$ Content | Weight Percent in Copolymer Mixture |
|---|---|
| a = 1 | 15.8 |
| a = 2 | 11.7 |
| a = 3 | 9.6 |
| a = 4 | 8.3 |
| a = 5 | 7.5 |
| a = 6 | 6.3 |
| a = 7 | 6.0 |
| a = 8 | 5.9 |
| a = 9 | 5.7 |
| a = 10 | 4.3 |
| a = 11 | 2.7 |
| a = 12 | 1.9 |
| a = 13 | 1.2 |
| a = 14 | 1.0 |

The vapor phase chromatographic analysis shows 6.8 percent by weight of the alkoxysiloxane copolymer is comprised of individual dimethylsiloxy ($OSiMe_2$) units possessing a value of a >10. The alkoxysiloxane copolymer is a clear liquid with a calculated molecular weight of 670. The alkoxysiloxane copolymer has the average composition.

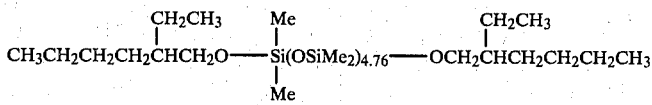

and is hereinafter referred to as Alkoxysiloxane Copolymer F.

EXAMPLE VII

PART A: PREPARATION OF ETHOXY END-BLOCKED SILOXANE FLUID

Into a 500 ml three-necked reaction flask equipped with a mechanical stirrer was added a mixture comprised of 44.4 grams (0.30 mole) of dimethyl diethoxysilane [$Me_2Si(OCH_2CH_3)_2$] and 165.2 grams (0.56 mole) of cyclic dimethylsiloxane tetramer ($Me_2SiO)_4$. Also added to the reaction flask was a potassium hydroxide catalyst in an amount corresponding to about one weight percent of the total weight of the mixture. The mixture was heated to a temperature of 130° C. and stirred for about four hours resulting in an equilibrated liquid product. The equilibrated liquid product was neutralized with acetic acid and then filtered through a pressure filter containing an average filter size of about 0.02 microns. The equilibrated liquid product, now properly designated an ethoxy end-blocked siloxane fluid, is a clear liquid with a viscosity of 6.68 cstk at a temperature of 25° C. The ethoxy content of the ethoxy end-blocked siloxane fluid is 12.1 percent by weight and the calculated molecular weight is 900. The ethoxy end-blocked siloxane fluid has the average composition,

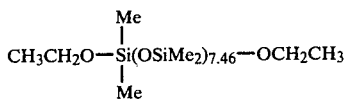

and is hereinafter referred to as Ethoxy End-Blocked Siloxane Fluid IV.

PART B: PREPARATION OF ALKOXYSILOXANE COPOLYMER

Into a 500 ml three-necked reaction flask equipped with a mechanical stirrer, thermometer, distillation column with head, and collecting flask was added 210.0 grams (0.23 mole) of Ethoxy End-Blocked Siloxane Fluid IV and 78.0 grams (0.60 mole) of 2-ethyl hexanol. To the reaction flask was also added a catalyst consisting of 0.5 weight percent trifluoroacetic acid and a solvent consisting of 50 weight percent toluene. The reaction mixture was heated to reflux at atmospheric pressure and a by-product ethanol as formed by transesterification. An ethanol-toluene azeotrope was removed from the reaction mixture upon heating the reaction mixture to reflux. When ethanol formation in the reaction flask had ceased, the remaining toluene was then removed by distillation. The product so produced was neutralized with sodium bicarbonate (NaHCO3) and filtered through a pressure filter containing an average filter size of 0.10 microns. The product is an alkoxysiloxane copolymer having a viscosity of 7.23 cstk at a temperature of 25° C. The alkoxysiloxane copolymer is a clear liquid with a calculated molecular weight of 870. The alkoxysiloxane copolymer has the average composition.

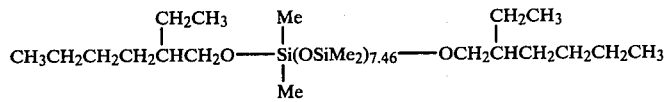

and is hereinafter referred to as Alkoxysiloxane Copolymer G.

EXAMPLE VIII

PART A: PREPARATION OF ETHOXY END-BLOCKED SILOXANE FLUID

Into a 500 ml three-necked reaction flask equipped with a mechanical stirrer was added a mixture comprised of 22.2 grams (0.15 mole) of dimethyl diethoxysilane [me2Si(OCH2CH3)2] and 127.8 grams (0.43 mole) of cyclic dimethylsiloxane tetramer (Me2SiO)4. Also added to the reaction flask was a potassium hydroxide catalyst in an amount corresponding to about one weight percent of the total weight of the mixture. The mixture was heated to a temperature of 130° C. and stirred for about four hours resulting in an equilibrated liquid product. The equilibrated liquid product was neutralized with acetic acid and then filtered through a pressure filter containing an average filter size of about 0.02 microns. The equilibrated liquid product, now properly designated an ethoxy end-blocked siloxane fluid, is a clear liquid with a viscosity of 10.21 cstk at a temperature of 25° C. The ethoxy content of the ethoxy end-blocked siloxane fluid is 8.7 percent by weight and the calculated molecular weight is 1000. The ethoxy end-blocked siloxane fluid has the average composition.

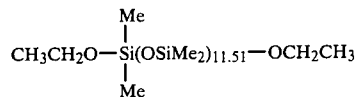

and is hereinafter referred to as Ethoxy End-Blocked Siloxane Fluid V.

PART B: PREPARATION OF ALKOXYSILOXANE COPOLYMER

Into a 500 ml three-necked reaction flask equipped with a mechanical stirrer, thermometer, distillation column with head, and collecting flask was added 250.0 grams (0.25 mole) of Ethoxy End-Blocked Siloxane Fluid V and 65.0 grams (0.50 mole) of 1-octanol. To the reaction flask was also added a catalyst consisting of 0.5 weight percent trifluoroacetic acid and a solvent consisting of 50 weight percent toluene. The reaction mixture was heated to reflux at atmospheric pressure and a by-product ethanol was formed by transesterifiction. An ethanol-toluene azeotrope was removed from the reaction mixture upon heating the reaction mixture to reflux. When ethanol formation in the reaction flask had ceased, the remaining toluene was removed by distillation. The product so produced was neutralized with sodium bicarbonate (NaHCO3) and filtered through a pressure filter containing an average filter size of 0.10 microns. The product is an alkoxysiloxane copolymer having a viscosity of 13.7 cstk at a temperature of 25° C. The alkoxysiloxane copolymer is a clear liquid with a calculated molecular weight of 1170. The alkoxysiloxane copolymer has the average composition,

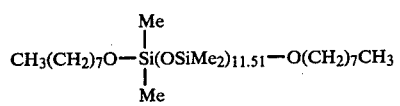

and is hereinafter referred to as Alkoxysiloxane Copolymer H.

EXAMPLE IX

PART A: PREPARATION OF ETHOXY END-BLOCKED SILOXANE FLUID

Into a 500 ml three-necked reaction flask equipped with a mechanical stirrer was added a mixture comprised of 62.3 grams (0.35 mole) of methyl triethoxysilane [MeSi(OCH2CH3)3] and 77.7 grams (0.26 mole) of cyclic dimethylsiloxane tetramer (Me2SiO)4. Also added to the reaction flask was a potassium hydroxide catalyst in an amount corresponding to about one weight percent of the total weight of the mixture. The mixture was heated to a temperature of 130° C. and stirred for about four hours resulting in an equilibrated liquid product. The equilibrated liquid product was neutralized with acetic acid and then filtered through a pressure filter containing an average filter size of about 0.02 microns. The equilibrated liquid product, now properly designated an ethoxy end-blocked siloxane fluid, is a clear liquid with a viscosity of 3.9 cstk at a temperature of 25° C. The ethoxy content of the ethoxy end-blocked siloxane fluid is 32.9 percent by weight and the calculated molecular weight is 400. The ethoxy end-blocked siloxane fluid has the average composition, $[MeSiO_{3/2}][Me_2SiO]_3[O\frac{1}{2}Ch_2CH_3]_3$ and is hereinafter referred to as Ethoxy End-Blocked Siloxane Fluid VI. The composition and properties of Ethoxy End-Blocked Siloxane Fluid VI and Ethoxy End-Blocked Siloxane Fluid VII described hereinafter are tabulated in Table IV below.

PART B: PREPRATION OF ALKOXYSILOXANE COPOLYMER

Into a 500 ml three-necked reaction flask equipped with a mechanical stirrer, thermometer, distillation column with head, and collecting flask was added 45.0 grams (0.11 mole) of Ethoxy End-Blocked Siloxane Fluid VI and 43.88 grams (0.34 mole) of 1-octanol. To the reaction flask was also added a catalyst consisting of 0.5 weight percent trifluoroacetic acid and a solvent consisting of 50 weight percent toluene. The reaction mixture was heated to reflux at atmospheric pressure and a by-product ethanol was formed by transesterification. An ethanol-toluene azeotrope was removed from the reaction mixture upon heating the reaction mixture to reflux. When ethanol formation in the reaction flask had ceased, the remaining toluene was removed by distillation. The product so produced was neutralized with sodium bicarbonate ($NaHCO_3$) and filtered through a pressure filter containing an average filter size of 0.10 microns. The product is an alkoxysiloxane copolymer having a viscosity of 3.92 cstk at a temperature of 25° C. The alkoxysiloxane copolymer is a clear liquid with a calculated molecular weight of 619. The alkoxysiloxane copolymer has the average composition,

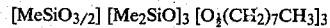

$[MeSiO_{3/2}][Me_2SiO]_3[O\frac{1}{2}(CH_2)_7CH_3]_3$ and is hereinafter referred to as Alkoxysiloxane Copolymer I. The composition and properties of Alkoxysiloxane Copolymer I and Alkoxysiloxane Copolymer J described hereinafter are tabulated in Table V below.

EXAMPLE X

PART A: PREPARATION OF ETHOXY END-BLOCKED SILOXANE FLUID

Into a 500 ml three-necked reaction flask equipped with a mechanical stirrer was added a mixture comprised of 62.3 grams (0.35 mole) of methyl triethoxysilane $[MeSi(OCH_2-CH_3)_3]$ and 155.4 grams (0.52 mole) of cyclic dimethylsiloxane tetramer $(Me_2SiO)_4$. Also added to the reaction flask was a potassium hydroxide catalyst in an amount corresponding to about one weight percent of the total weight of the mixture. The mixture was heated to a temperature of 130° C. and stirred for about four hours resulting in an equilibrated liquid product. The equilibrated liquid product was neutralized with acetic acid and then filtered through a pressure filter containing an average filter size of about 0.02 microns. The equilibrated liquid product, now properly designated an ethoxy end-blocked siloxane fluid, is a clear liquid with a viscosity of 6.21 cstk at a temperature of 25° C. The ethoxy content of the ethoxy end-blocked siloxane fluid is 21.7 percent by weight and the calculated molecular weight is 622. The ethoxy end-blocked siloxane fluid has the average composition,

$[MeSiO_{3/2}][Me_2SiO]_6[O\frac{1}{2}CH_2CH_3]_3$ and is hereinafter referred to as Ethoxy End-Blocked Siloxane Fluid VII.

PART B: PREPARATION OF ALKOXYSILOXANE COPOLYMER

Into a 500 ml three-necked reaction flask equipped with a mechanical stirrer, thermometer, distillation column with head, and collecting flask was added 217.7 grams (0.35 mole) of Ethoxy End-Blocked Siloxane Fluid VII and 106.1 grams (1.05 mole) of 1-hexanol. To the reaction flask was also added a catalyst consisting of 0.5 weight percent trifluoroacetic acid and a solvent consisting of 50 weight percent toluene. The reaction mixture was heated to reflux at atmospheric pressure and a by-product ethanol was formed by transesterification. An ethanol-toluene azeotrope was removed from the reaction mixture upon heating the reaction mixture to reflux. When ethanol formation in the reaction flask had ceased, the remaining toluene was removed by distillation. The product so produced was neutralized with sodium bicarbonate ($NaHCO_3$) and filtered through a pressure filter containing an average filter size of 0.10 microns. The product is an alkoxysiloxane copolymer having a viscosity of 9.32 cstk at a temperature of 25° C. The alkoxysiloxane copolymer is a clear liquid with a calculated molecular weight of 790. The alkoxysiloxane copolymer has the average composition,

$[MeSiO_{3/2}][Me_2SiO]_6[O\frac{1}{2}(CH_2)_5CH_3]_3$ and is hereinafter referred to as Alkoxysiloxane Copolymer J.

EXAMPLE XI

PREPARATION OF ALKOXYSILOXANE COPOLYMER MIXTURE

An alkoxysiloxane copolymer mixture was prepared by mixing a surfactant solution containing Alkoxysiloxane Copolymer D and a surfactant solution containing Alkoxysiloxane Copolymer I. These surfactant solutions were mixed in a ratio of 0.75 parts of the surfactant solution containing Alkoxysiloxane Copolymer D to 0.25 parts of the surfactant solution containing Alkoxysiloxane Copolymer I. The resulting alkoxysiloxane copolymer mixture contained 75 percent by weight of Alkoxysiloxane Copolymer D and 25 percent by weight of Alkoxysiloxane Copolymer I. This mixture is hereinafter referred to as Alkoxysiloxane Copolymer Mixture K. The composition and properties of Alkoxysiloxane Copolymer Mixture K and Alkoxysiloxane Copolymer Mixture L described hereinafter are tabulated in Table VI below.

EXAMPLE XII

PREPARATION OF ALKOXYSILOXANE COPOLYMER MIXTURE

An alkoxysiloxane copolymer mixture was prepared by mixing a surfactant solution containing alkoxysiloxane Copolymer D and a surfactant solution containing Alkoxysiloxane Copolymer I. These surfactant solutions were mixed in a ratio of 0.50 parts of the surfactant solution containing Alkoxysiloxane Copolymer D to 0.50 parts of the surfactant solution containing Alkoxysiloxane Copolymer I. The resulting alkoxysiloxane copolymer mixture contained 50 percent by weight of Alkoxysiloxane Copolymer D and 50 percent by weight of Alkoxysiloxane Copolymer I. This mixture is hereinafter referred to as Alkoxysiloxane Copolymer Mixture L.

EXAMPLES XIII through XXXII

In accordance with these examples, high resilience polyurethane foams were produced using the above described alkoxysilane monomer, alkoxysiloxane copolymers and alkoxysiloxane copolymer mixtures as the foam stabilizing surfactant component of the foam-producing reaction mixtures. For the purpose of comparison, three commercially available foam stabilizing surfactants outside the scope of this invention were used and are designated herein as Organosiloxane Copolymer MM, Organosiloxane Copolymer NN and Organosiloxane Copolymer OO. These foam stabilizing surfactants have the following average composition:

Organosiloxane Copolymer MM

A high resilience foam surfactant within the scope of U.S. Pat. No. 3,741,917.

Organosiloxane Copolymer NN

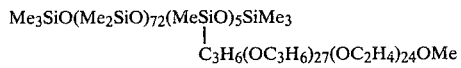

(A hot cure flexible foam surfactant)

Organosiloxane Copolymer OO

Me$_3$SiO(Me$_2$SiO)$_3$SiMe$_3$ (A 5 cstk dimethyl siloxane oil-molecular species distribution unknown).

Additionally, five other foam stabilizing surfactants outside the scope of this invention were used for the purpose of comparison and are designated herein as Alkoxysilane Monomer PP, Alkoxysiloxane Copolymer QQ, Alkoxysiloxane Copolymer RR, Alkoxysiloxane Copolymer SS and Alkoxysiloxane Copolymer TT. These alkoxy-modified foam stabilizing surfactants were undistilled and have the following average composition.

Alkoxysilane Monomer PP

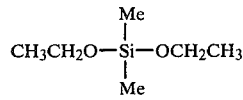

(An alkoxysilane monomer with 2 carbon atoms in each alkoxy group)

Alkoxysiloxane Copolymer QQ

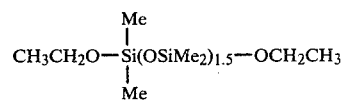

(An alkoxysiloxane copolymer with 2 carbon atoms in each alkoxy group)

Alkoxysiloxane Copolymer RR

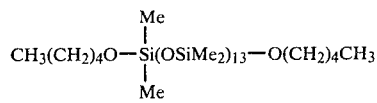

(A cold cure high resilience foam surfactant with 13 dimethylsiloxy groups)

Alkoxysiloxane Copolymer SS

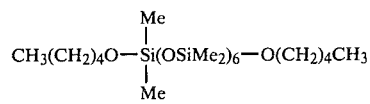

(A cold cure high resilience foam surfactant with 5 carbon atoms in each alkoxy group)

Alkoxysiloxane Copolymer TT

[MeSiO$_{3/2}$][Me$_2$SiO]$_6$[O$\frac{1}{2}$CH$_2$CH$_3$]$_3$ (A cold cure high resilience foam surfactant with 2 carbon atoms in each alkoxy group)

Experience in the field of low density high resilience polyurethane foam formulation has demonstrated a need for a foam stabilizing surfactant having wide processing latitude. For example, when surface defects appear in low density high resilience polyurethane foam, an increased amount of foam stabilizing surfactant is applied to remedy this problem. However, increasing the amount of foam stabilizing surfactant in low density high resilience polyurethane foam formulation will result in shrinkage of the foam. Therefore, a foam stabilizing surfactant having wide processing latitude is essential for overcoming the variations encountered in low density high resilience polyurethane foam formulation. While certain of the above identified comparative foam stabilizing surfactants outside the scope of this invention perform adequately at a very narrow concentration range, they do not perform adequately in view of overcoming the many variations encountered in formulating low density high resilience polyurethane foam.

The composition of the foam-producing reaction mixtures are given below in Table A.

TABLE A

| FOAM FORMULATIONS | |
|---|---|
| Ingredients | Low Density Foam (PHPP) |
| Polyol I | 60 |
| Polyol II | 40 |
| Polymer/Polyol I | — |
| Catalyst I | 0.15 |
| H$_2$O | 3.5 |
| Catalyst II | — |
| Catalyst III | 0.50 |
| Catalyst IV | — |
| Polyol I | — |
| Catalyst V | 0.10 |
| Alkoxysilicon Composition Surfactant | Varied |
| Catalyst VI | 1.7 |
| Blowing Agent I | 7.0 |
| Isocyanate I | 44.7 |
| Isocyanate II | — |
| Flame Retardant I | 2.0 |

The foam-producing reactions of Examples XIII through XXXII were carried out in accordance with substantially the same general procedure which entailed the following steps. The alkoxysilicon composition surfactant and dibutyltindilaurate were premixed and dispersed with a spatula. The polyols and polymer/polyol of Table A were premixed and 250 grams were dispersed in a Lily cup. The alkoxysilicon composition surfactant/dibutyltindilaurate premix was added by a five cc syringe into the polyol-polymer/polyol premix and dispersed with a spatula until homogeneous, forming a polyol/surfactant blend in the Lily cup. A premix consisting of water, blowing agent and the remaining catalysts of Table A was added to the polyol/surfactant blend and dispersed with a spatula in the Lily cup until homogeneous. The Lily up containing the foaming components was placed under a drill press equipped with a double three-bladed marine-type propeller about three inches in diameter. The mixing in the drill press was accomplished at 2150 revolutions per minute for ten seconds. Due to the high viscosity of the polyol-polymer/polyol mixture, the Lily cup must be moved around to insure proper mixing. Then the isocyanate was added rapidly to the other components without stopping the drill press and mixing continued for another seven seconds. The reaction mixture was immediately poured into an 8 in.×8 in.×6 in. cake box supported by a wooden mold and allowed to rise. The foam was allowed to rest in the cake box for two minutes after completion of the rise to avoid densification at the bottom of the foam bun. The foam was then cured for about ten minutes at 125° C. and samples of the foam products were prepared for experimental evaluations.

The alkoxysilicon composition surfactants represented by Formula (I), Formula (II) and Formula (III) of this invention were employed as a solution in the formulation of polyurethane foam. The solution consisted of 10.0 weight percent alkoxysilicon composition surfactant and 90.0 weight percent Polyol I. The comparative organosiloxane copolymer surfactants, alkoxysilane monomer surfactant, and alkoxysiloxane copolymer surfactants outside the scope of this invention were also employed as a solution in the formulation of polyurethane foam. Organosiloxane Copolymer MM was employed in a solution consisting of 10 to 35 weight percent organosiloxane copolymer and 65 to 90 weight percent polyol solvent. Organosiloxane Copolymer NN was employed in a solution consisting of 40 to 60 weight percent organosiloxane copolymer and 40 to 60 weight percent polyol solvent. Organosiloxane Copolymer OO was not employed as a solution in the formulation of polyurethane foam. Alkoxysilane Monomer PP was employed in a solution consisting of 10.0 weight percent alkoxysilane monomer and 90.0 weight percent Polyol I. Alkoxysiloxane Copolymers QQ, RR, SS, and TT were likewise employed in a solution consisting of 10.0 weight percent alkoxysiloxane copolymer and 90.0 weight percent Polyol I.

The results of examples in which alkoxysilane monomers of the type represented by Formula (I) above are utilized as the foam stabilizing surfactant component of the foam-producing reaction mixture are given in Table B below.

TABLE B

EVALUATION OF ALKOXYSILANE MONOMERS (FORMULA I TYPE)

| EXAMPLE | ALKOXYSILANE MONOMER | ALKOXYSILANE MONOMER STRUCTURE | CONCENTRATION* (PHPP) | COARSE CELLS | SHRINKAGE |
|---|---|---|---|---|---|
| XIII | A | $CH_3(CH_2)_7O-\underset{\underset{Me}{\|}}{\overset{\overset{Me}{\|}}{Si}}-O(CH_2)_7CH_3$ | 2.0 | Slight | None |
|  |  |  | 5.0 | None | None |
|  |  |  | 7.0 | None | None |
|  |  |  | 10.0 | None | None |
| XIV | B | $CH_3(CH_2)_{10}O-\underset{\underset{Me}{\|}}{\overset{\overset{Me}{\|}}{Si}}-O(CH_2)_{10}CH_3$ | 1.3 | Slight | None |
|  |  |  | 2.0 | None | None |
|  |  |  | 2.5 | None | Slight |
| XV | C | $CH_3(CH_2)_{15}O-\underset{\underset{Me}{\|}}{\overset{\overset{Me}{\|}}{Si}}-O(CH_2)_{15}CH_3$ | 0.75 | Slight | None |
|  |  |  | 1.0 | None | None |
|  |  |  | 1.7 | None | None |
|  |  |  | 2.0 | None | None |
|  |  |  | 3.5 | None | Slight |
| XVI** | PP | $CH_3CH_2O-\underset{\underset{Me}{\|}}{\overset{\overset{Me}{\|}}{Si}}-OCH_2CH_3$ | 5.0 | Coarse | None |
|  |  |  | 7.0 | Coarse | None |
|  |  |  | 10.0 | Coarse | None |

*Concentration of surfactant solution.
**Outside scope of this invention.

The data of Table B demonstrates that the alkoxysilane monomers are effective stabilizers in high resilience polyurethane foam formulations.

The results of examples in which alkoxysiloxane copolymers of the type represented by formula (II) above are utilized as the foam stabilizing surfactant component of the foam-producing reaction mixture are given in Table C below.

TABLE C

EVALUATION OF ALKOXYSILOXANE COPOLYMERS (FORMULA II TYPE)

| EXAMPLE | ALKOXYSILOXANE COPOLYMER | ALKOXYSILOXANE COPOLYMER STRUCTURE | CONCENTRATION* (PHPP) | COARSE CELLS | SHRINKAGE |
|---|---|---|---|---|---|
| XVII | D | $CH_3(CH_2)_7O-Si(OSiMe_2)_{2.0}-O(CH_2)_7CH_3$ with Me, Me substituents | 0.5 | Very Slight | None |
|  |  |  | 0.75 | Slight | None |
|  |  |  | 1.0 | None | None |
|  |  |  | 5.0 | None | None |
|  |  |  | 10.0 | None | None |
|  |  |  | 12.0 | None | None |
|  |  |  |  | None |  |
| XVIII | E | $CH_3(CH_2)_5O-Si(OSiMe_2)_{3.0}-O(CH_2)_5CH_3$ with Me, Me substituents | 0.2 | Slight | None |
|  |  |  | 0.5 | None | None |
|  |  |  | 0.75 | None | None |
|  |  |  | 1.0 | None | None |
|  |  |  | 5.0 | None | None |
|  |  |  | 8.0 | None | None |
|  |  |  | 8.5 | None | Very Slight |
| XIX | F | $CH_3(CH_2)_3CHCH_2O-Si(OSiMe_2)_{4.76}-OCH_2CH(CH_2)_3CH_3$ with $CH_2CH_3$, Me, $CH_2CH_3$, Me substituents | 0.01 | Very Slight | None |
|  |  |  | 0.03 | Slight | None |
|  |  |  | 0.1 | None | None |
|  |  |  | 0.5 | None | None |
|  |  |  | 2.0 | None | None |
|  |  |  | 2.5 | None | Very Slight |
|  |  |  |  | None | Slight |
| XX | G | $CH_3(CH_2)_3CHCH_2O-Si(OSiMe_2)_{7.46}-OCH_2CH(CH_2)_3CH_3$ with $CH_2CH_3$, Me, $CH_2CH_3$, Me substituents | 0.01 | None | None |
|  |  |  | 0.02 | None | None |
|  |  |  | 0.1 | None | None |
|  |  |  | 1.0 | None | None |
|  |  |  | 1.25 | None | Very Slight |
| XXI | H | $CH_3(CH_2)_7O-Si(OSiMe_2)_{11.51}-O(CH_2)_7CH_3$ with Me, Me substituents | 0.01 | None | None |
|  |  |  | 0.05 | None | None |
|  |  |  | 0.1 | None | None |
|  |  |  | 0.8 | None | Very Slight |
| XXII** | MM | A high resiliency foam surfactant within the scope of U.S. Pat. No. 3,741,917. | 0.75 | Coarse | None |
|  |  |  | 1.0 | None | None |
|  |  |  | 1.5 | None | None |
|  |  |  | 2.5 | None | Slight |
| XXIII** | NN | $Me_3SiO(Me_2SiO)_{72}(MeSiO)_5SiMe_3$ with $C_3H_6(OC_3H_6)_{27}(OC_2H_4)_{24}OMe$ | 0.01 | None | Severe |
|  |  |  | 0.05 | None | Severe |
| XXIV** | OO | $Me_3SiO(Me_2SiO)_3SiMe_3$ | 0.1 | Very Coarse | None |
|  |  |  | 0.5 | Very Coarse | None |
|  |  |  | 1.0 | Very Coarse | None |
|  |  |  | 2.0 | Very Coarse | None |
|  |  |  | 4.0 | Very Coarse | None |
|  |  |  | 5.0 | Very Coarse | None |
| XXV** | QQ | $CH_3CH_2O-Si(OSiMe_2)_{1.5}-OCH_2CH_3$ with Me, Me substituents | 0.5 | Coarse | None |
|  |  |  | 1.0 | Coarse | None |
|  |  |  | 1.5 | Very Slight | None |
|  |  |  | 2.5 | None | None |
|  |  |  | 5.5 | None | None |
|  |  |  | 7.5 | None | ***Glossy Appearance |
|  |  |  | 10.0 | None | ***Glossy Appearance |
| XXVI** | RR | $CH_3(CH_2)_4O-Si(OSiMe_2)_{13}-O(CH_2)_4CH_3$ with Me, Me substituents | 0.1 | Very Slight | None |
|  |  |  | 0.2 | None | Slight |
|  |  |  | 0.3 | None | Moderate |
|  |  |  | 0.5 | None | Severe |

TABLE C-continued
EVALUATION OF ALKOXYSILOXANE COPOLYMERS (FORMULA II TYPE)

| EXAMPLE | ALKOXYSILOXANE COPOLYMER | ALKOXYSILOXANE COPOLYMER STRUCTURE | CONCENTRATION* (PHPP) | COARSE CELLS | SHRINKAGE |
|---|---|---|---|---|---|
| XXVII** | SS | $CH_3(CH_2)_4O-\underset{\underset{Me}{\|}}{\overset{\overset{Me}{\|}}{Si}}(OSiMe_2)_6-O(CH_2)_4CH_3$ | 0.1 | Slight | None |
|  |  |  | 0.2 | None | None |
|  |  |  | 0.35 | None | Severe |

*Concentration of surfactant solution.
**Outside the scope of this invention.
***Glossy appearance is indicative of poor quality foam.

The data of Table C demonstrates that the alkoxysiloxane copolymers are effective stabilizers in high resilience polyurethane foam formulations.

The results of examples in which alkoxysiloxane copolymers of the type represented by Formula (III) above are utilized as the foam stabilizing surfactant component of the foam producing reaction mixture are given in Table D below.

The data of Table D demonstrates that the alkoxysiloxane copolymers are effective stabilizers in high resilience polyurethane form formulations.

The results of examples in which alkoxysiloxane copolymer mixtures are utilized as the foam stabilizing surfactant component of the foam-producing reaction mixture are given in Table E below.

TABLE D
EVALUATION OF ALKOXYSILOXANE COPOLYMERS (FORMULA III TYPE)

| EXAMPLE | ALKOXYSILOXANE COPOLYMER | ALKOXYSILOXANE COPOLYMER STRUCTURE | CONCENTRATION* (PHPP) | COARSE CELLS | SHRINKAGE |
|---|---|---|---|---|---|
| XXVIII | I | $[MeSiO_{3/2}][Me_2SiO]_3[O_{\frac{1}{2}}(CH_2)_7CH_3]_3$ | 0.05 | Very Slight | None |
|  |  |  | 0.1 | None | None |
|  |  |  | 0.75 | None | None |
|  |  |  | 1.0 | None | None |
|  |  |  | 2.5 | None | None |
|  |  |  | 3.0 | None | Very Slight |
| XXIX | J | $[MeSiO_{3/2}][Me_2SiO]_6[O_{178}(CH_2)_5CH_3]_3$ | 0.1 | Slight | None |
|  |  |  | 0.2 | None | None |
|  |  |  | 0.5 | None | None |
|  |  |  | 1.0 | None | None |
|  |  |  | 1.5 | None | None |
|  |  |  | 3.5 | None | None |
|  |  |  | 5.0 | None | None |
|  |  |  | 5.5 | None | Slight |
| XXX** | TT | $[MeSiO_{3/2}][Me_2SiO]_6[O_{\frac{1}{2}}CH_2CH_3]_3$ | 0.1 | Coarse | None |
|  |  |  | 0.2 | None | None |
|  |  |  | 0.3 | None | Slight |
|  |  |  | 0.4 | None | Severe |

* Concentration of surfactant solution.
** Outside scope of this invention.

TABLE E
EVALUATION OF ALKOXYSILOXANE COPOLYMER MIXTURES

| EXAMPLE | ALKOXYSILOXANE COPOLYMER MIXTURE | ALKOXYSILOXANE COPOLYMER MIXTURE STRUCTURE | CONCENTRATION* (PHPP) | COARSE CELLS | SHRINKAGE |
|---|---|---|---|---|---|
| XXXI | K | $CH_3(CH_2)_7O-\underset{\underset{Me}{\|}}{\overset{\overset{Me}{\|}}{Si}}(OSiMe_2)_{2.0}-O(CH_2)_7CH_3$ <br><br> $[MeSiO_{3/2}][Me_2SiO]_3[O_{\frac{1}{2}}(CH_2)_7CH_3]_3$ <br> (25 weight percent) | 0.1 | Slight | None |
|  |  |  | 0.3 | None | None |
|  |  |  | 0.5 | None | None |
|  |  |  | 1.0 | None | None |
|  |  |  | 2.0 | None | None |
|  |  |  | 3.0 | None | None |
|  |  |  | 5.0 | None | None |
|  |  |  | 7.0 | None | None |
|  |  |  | 8.0 | None | None |
|  |  |  | 8.5 | None | Slight |
| XXXII | L | $CH_3(CH_2)_7O-\underset{\underset{Me}{\|}}{\overset{\overset{Me}{\|}}{Si}}(OSiMe_2)_{2.0}-O(CH_2)_7CH_3$ <br><br> $[MeSiO_{3/2}][Me_2SiO]_3[O_{\frac{1}{2}}(CH_2)_7CH_3]_3$ <br> (50 weight percent) | 0.1 | None | None |
|  |  |  | 1.0 | None | None |
|  |  |  | 2.5 | None | None |
|  |  |  | 3.5 | None | None |
|  |  |  | 4.5 | None | None |
|  |  |  | 5.0 | None | None |
|  |  |  | 6.0 | None | None |
|  |  |  | 6.5 | None | Slight |

*Concentration of surfactant solution.

The data of Table E demonstrates that alkoxysiloxane copolymer mixtures are effective stabilizers in high resilience polyurethane foam formulations.

EXAMPLES XXXIII and XXXIV

Alkoxysiloxane Copolymer D and Alkoxysiloxane Copolymer I were evaluated on an industrial scale machine as a foam stabilizing surfactant component in the formulation of high resilience polyurethane foam. The molding and free rise conditions of the industrial scale machine are described in Table F below.

The results of utilizing Alkoxysiloxane Copolymer D and Alkoxysiloxane Copolymer I as a foam stabilizing surfactant component for the formulation of high resilience polyurethane foam employing an industrial scale machine are described in Table G below.

TABLE G
EVALUATION OF ALKOXYSILOXANE COPOLYMER D AND ALKOXYSILOXANE COPOLYMER I ON INDUSTRIAL SCALE MACHINE

| EXAMPLE | ALKOXYSILOXANE COPOLYMER | ALKOXYSILOXANE COPOLYMER STRUCTURE | CONCENTRATION* (PHPP) | COARSE CELLS | SHRINKAGE |
|---|---|---|---|---|---|
| XXXIII | D | $CH_3(CH_2)_7O-Si(OSiMe_2)_{2.0}-O(CH_2)_7CH_3$ with Me groups on Si | 0.4 | Slight | None |
| | | | 0.5 | Very Slight | None |
| | | | 0.8 | None | None |
| | | | 1.0 | None | None |
| | | | 1.25 | None | None |
| | | | 1.5 | None | None |
| | | | 1.75 | None | None |
| | | | 2.0 | None | None |
| XXXIV | I | $[MeSiO_{3/2}][Me_2SiO]_3[O_{\frac{1}{2}}(CH_2)_7CH_3]_3$ | 0.1 | Slight | None |
| | | | 0.2 | Very Slight | None |
| | | | 0.4 | None | None |
| | | | 1.0 | None | None |
| | | | 1.5 | None | None |

*Concentration of surfactant solution.

The data of Table G demonstrates that Alkoxysiloxane Copolymer D and Alkoxysiloxane Copolymer I are also effective stabilizers for high resilience polyurethane foam formulated in an industrial scale machine.

TABLE F
MOLDING AND FREE RISE CONDITIONS

| Conditions | I | II |
|---|---|---|
| Machine | Admiral 170 lb./min. | Admiral 170 lb./min. |
| Metal to Metal Seal | ¼ in. vent holes | Sealed 1/16 in. vent holes |
| Mixer Speed | 4500 RPM | 4500 RPM |
| Ambient Temperature | 75° C. | 75° C. |
| Pour Time | 3.4–3.7 seconds | 3.4–3.7 seconds |
| Release Agent | Brulins Wax | Brulins Wax |
| Soak Time | 5 minutes | 5 minutes |
| Past Cure | 2 minutes at room temperature | 2 minutes Infrared |
| Pad Weight | 3700–3800 grams | 3700–3800 grams |
| Conveyor Speed | 70 ft./min. | 70 ft./min. |
| Order No. | 5100 | 5100 |
| Reference No. | BA-121,122 | BA-121,122 |

TABLE I
ALKOXYSILANE MONOMERS (FORMULA I TYPE)

| Alkoxysilane Monomer | Alkoxysilane Monomer Structure | Molecular Weight | Viscosity at 25° C. (cstk) |
|---|---|---|---|
| A | $CH_3(CH_2)_7O-Si(Me)(Me)-O(CH_2)_7CH_3$ | 316 | 5.9 |
| B | $CH_3(CH_2)_{10}O-Si(Me)(Me)-O(CH_2)_{10}CH_3$ | 403 | 14.8 |
| C | $CH_3(CH_2)_{15}O-Si(Me)(Me)-O(CH_2)_{15}CH_3$ | 543 | 21.17 |

TABLE II
ETHOXY END-BLOCKED SILOXANE FLUIDS (FORMULA II TYPE)

| Ethoxy End-Blocked Siloxane Fluid | Ethoxy End-Blocked Siloxane Fluid Structure | Molecular Weight | Viscosity at 25° C. (cstk) | Ethoxy Content (wt. %) |
|---|---|---|---|---|
| I | $CH_3CH_2O-Si(Me)(Me)(OSiMe_2)_{2.0}-OCH_2CH_3$ | 296 | 1.64 | 29.2 |
| II | $CH_3CH_2O-Si(Me)(Me)(OSiMe_2)_{3.0}-OCH_2CH_3$ | 370 | 2.54 | 24.0 |
| III | $CH_3CH_2O-Si(Me)(Me)(OSiMe_2)_{4.76}-OCH_2CH_3$ | 500 | 3.83 | 17.1 |
| IV | $CH_3CH_2O-Si(Me)(Me)(OSiMe)_{7.46}-OCH_2CH_3$ | 900 | 6.68 | 12.1 |

TABLE II-continued
ETHOXY END-BLOCKED SILOXANE FLUIDS (FORMULA II TYPE)

| Ethoxy End-Blocked Siloxane Fluid | Ethoxy End-Blocked Siloxane Fluid Structure | Molecular Weight | Viscosity at 25° C. (cstk) | Ethoxy Content (wt. %) |
|---|---|---|---|---|
| V | $CH_3CH_2O-\underset{\underset{Me}{\mid}}{\overset{\overset{Me}{\mid}}{Si}}(OSiMe_2)_{11.51}-OCH_2CH_3$ | 1000 | 10.21 | 8.7 |

TABLE III
ALKOXYSILOXANE COPOLYMERS (FORMULA II TYPE)

| ALKOXYSILOXANE COPOLYMER | ALKOXYSILOXANE COPOLYMER STRUCTURE | MOLECULAR WEIGHT | VISCOSITY at 25° C. (cstk) |
|---|---|---|---|
| D | $CH_3(CH_2)_7O-\underset{\underset{Me}{\mid}}{\overset{\overset{Me}{\mid}}{Si}}(OSiMe_2)_{2.0}-O(CH_2)_7CH_3$ | 466 | 4.82 |
| E | $CH_3(CH_2)_5O-\underset{\underset{Me}{\mid}}{\overset{\overset{Me}{\mid}}{Si}}(OSiMe_2)_{3.0}-O(CH_2)_5CH_3$ | 482 | 5.12 |
| F | $m\ CH_3(CH_2)_3\overset{\overset{CH_2CH_3}{\mid}}{C}HCH_2O-\underset{\underset{Me}{\mid}}{\overset{\overset{Me}{\mid}}{Si}}(OSiMe_2)_{4.76}-O\overset{\overset{CH_2CH_3}{\mid}}{C}HCH_2(CH_2)_3CH_3$ | 670 | 6.34 |
| G | $CH_3(CH_2)_3\overset{\overset{CH_2CH_3}{\mid}}{C}HCH_2O-\underset{\underset{Me}{\mid}}{\overset{\overset{Me}{\mid}}{Si}}(OSiMe_2)_{7.46}-OCH_2\overset{\overset{CH_2CH_3}{\mid}}{C}H(CH_2)_3CH_3$ | 870 | 7.23 |
| H | $CH_3(CH_2)_7O-\underset{\underset{Me}{\mid}}{\overset{\overset{Me}{\mid}}{Si}}(OSiMe_2)_{11.51}-O(CH_2)_7CH_3$ | 1170 | 13.7 |

TABLE IV
ETHOXY END-BLOCKED SILOXANE FLUIDS (FORMULA III TYPE)

| Ethoxy End-Blocked Siloxane Fluid | Ethoxy End-Blocked Siloxane Fluid Structure | Molecular Weight | Viscosity at 25° C. (cstk) | Ethoxy Content (wt. percent) |
|---|---|---|---|---|
| VI | $[MeSiO_{3/2}][Me_2SiO]_3[O_{\frac{1}{2}}CH_2CH_3]_3$ | 400 | 3.9 | 32.9 |
| VII | $[MeSiO_{3/2}][Me_2SiO]_6[O_{\frac{1}{2}}CH_2CH_3]_3$ | 622 | 6.21 | 21.7 |

TABLE V
ALKOXYSILOXANE COPOLYMERS (FORMULA III TYPE)

| Alkoxysiloxane Co-polymer | Alkoxysiloxane Copolymer Structure | Molecular Weight | Viscosity at 25° C. (cstk) |
|---|---|---|---|
| I | $[MeSiO_{3/2}][Me_2SiO]_3[O_{\frac{1}{2}}(CH_2)_7CH_3]_3$ | 619 | 3.92 |
| J | $[MeSiO_{3/2}][Me_2SiO]_6[O_{\frac{1}{2}}(CH_2)_5CH_3]_3$ | 790 | 9.32 |

TABLE VI
ALKOXYSILOXANE COPOLYMER MIXTURES

| Alkoxysiloxane Copolymer Mixture | Alkoxysiloxane Copolymer Mixture Structure | Surfactant Solution Mixture Ratio (parts) | Alkoxysiloxane Copolymer Mixture Ratio (wt. %) |
|---|---|---|---|
| K | $CH_3(CH_2)_7O-\underset{\underset{Me}{\mid}}{\overset{\overset{Me}{\mid}}{Si}}(OSiMe_2)_{2.0}-O(CH_2)_7CH_3$ | .75 | 75 |
|   | $[MeSiO_{3/2}][Me_2SiO]_3[O_{\frac{1}{2}}(CH_2)_7CH_3]_3$ | .25 | 25 |
| L | $CH_3(CH_2)_7O-\underset{\underset{Me}{\mid}}{\overset{\overset{Me}{\mid}}{Si}}(OSiMe_2)_{2.0}-O(CH_2)_7CH_3$ | .50 | 50 |

TABLE VI-continued
ALKOXYSILOXANE COPOLYMER MIXTURES

| Alkoxysiloxane Copolymer Mixture | Alkoxysiloxane Copolymer Mixture Structure | Surfactant Solution Mixture Ratio (parts) | Alkoxysiloxane Copolymer Mixture Ratio (wt. %) |
|---|---|---|---|
| | [MeSiO$_{3/2}$][O$_{\frac{1}{2}}$(CH$_2$)$_7$CH$_3$]$_3$ | | |

What is claimed is:

1. A process for producing high resilience polyurethane foam having a density no greater than 2.0 pounds per cubic foot which comprises simultaneously reacting and foaming a reaction mixture containing: (a) an organic polyol selected from the group consisting of (i) a polyether triol containing at least 40 mole percent primary hydroxyl groups and having a molecular weight from about 2,000 to about 8,000 and (ii) a mixture of said polyether triol and other polyethers having an average of at least two hydroxyl groups, said polyether triol of said mixture amounting to at least 40 weight percent of the total polyol content; (b) a polyisocyanate, said organic polyol and said polyisocyanate being present in the mixture in a major amount and in a relative amount required to produce the polyurethane foam; (c) a blowing agent in a minor amount sufficient to foam the reaction mixture; (d) a catalytic amount of catalysts for the production of polyurethane foam; and (e) as a foam stabilizer, an alkoxysilicon composition selected from the group consisting of:

(I) an alkoxysilane monomer having the average formula;

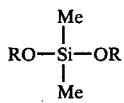

wherein Me is a methyl group and R is an alkyl group having from 6 to 18 carbon atoms inclusive;

(II) an alkoxysiloxane copolymer having the average formula;

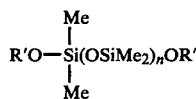

wherein Me is a methyl group, R' is an alkyl group having from 7 to 18 carbon atoms inclusive in which the R' groups represent from 15 to 75 weight percent of the alkoxysiloxane copolymer, and n has an average value from one to twelve inclusive; and (III) an alkoxysiloxane copolymer having the average formula;

wherein Me is a methyl group, R" is an alkyl group having from 5 to 18 carbon atoms inclusive in which the R" groups represent from 15 to 70 weight percent of the alkoxysiloxane copolymer, x has an average value from one to three inclusive, y has an average value from zero to (18-x) inclusive, and z has an average value from 3 to 5 inclusive.

2. The high resilience polyurethane foam produced by the process as defined in claim 1.

3. A process for producing high resilience polyurethane foam having a density no greater than 2.0 pounds per cubic foot which comprises simultaneously reacting and foaming a reaction mixture containing: (a) an organic polyol selected from the group consisting of (i) a polyether triol containing at least 40 mole percent primary hydroxyl groups and having a molecular weight from about 2,000 to about 8,000 and (ii) a mixture of said polyether triol and other polyethers having an average of at least two hydroxyl groups, said polyether triol of said mixture amounting to at least 40 weight percent of the total polyol content; (b) a polyisocyanate, said organic polyol and said polyisocyanate being present in the mixture in a major amount and in a relative amount required to produce the polyurethane foam; (c) a blowing agent in a minor amount sufficient to foam the reaction mixture; (d) a catalytic amount of catalysts for the production of polyurethane foam; and (e) a foam stabilizer comprising an alkoxysilane monomer having the average composition,

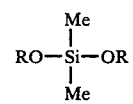

wherein Me is a methyl group and R is an alkyl group having from 6 to 18 carbon atoms inclusive.

4. The high resilience polyurethane foam produced by the process as defined in claim 3.

5. A process for producing high resilience polyurethane foam having a density of no greater than 2.0 pounds per cubic foot which comprises simultaneously reacting and foaming a reaction mixture containing: (a) an organic polyol selected from the group consisting of (i) a polyether triol containing at least 40 mole percent primary hydroxyl groups and having a molecular weight from about 2,000 to about 8,000 and (ii) a mixture of said polyether triol and other polyethers having an average of at least two hydroxyl groups, said polyether triol of said mixture amounting to at least 40 weight percent of the total polyol content; (b) a polyisocyanate, said organic polyol and said polyisocyanate being present in the mixture in a major amount and in a relative amount required to produce the polyurethane foam; (c) a blowing agent in a minor amount sufficient to foam the reaction mixture; (d) a catalytic amount of catalysts for the production of polyurethane foam; and (e) a foam stabilizer comprising an alkoxysiloxane copolymer having the average composition

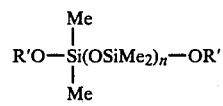

wherein Me is a methyl group, R' is an alkyl group having from 7 to 18 carbon atoms inclusive, the R' groups represent from 15 to 75 weight percent of the alkoxysiloxane copolymer, and n has an average value from one to 12 inclusive.

6. The high resilience polyurethane foam produced by the process as defined in claim 5.

7. A process for producing high resilience polyurethane foam having a density of no greater than 2.0 pounds per cubic foot which comprises simultaneously reacting and foaming a reaction mixture containing: (a) an organic polyol selected from the group consisting of (i) a polyether triol containing at least 40 mole percent primary hydroxyl groups and having a molecular weight from about 2,000 to about 8,000 and (ii) a mixture of said polyether triol and other polyethers having an average of at least two hydroxyl groups, said polyether triol of said mixture amounting to at least 40 weight percent of the total polyol content; (b) a polyisocyanate, said organic polyol and said polyisocyanate being present in the mixture in a major amount and in a relative amount required to produce the polyurethane foam; (c) a blowing agent in a minor amount sufficient to foam the reaction mixture; (d) a catalytic amount of catalysts for the production of polyurethane foam; and (e) a foam stabilizer comprising an alkoxysiloxane copolymer having the average composition,

$[MeSiO_{3/2}]_x[Me_2SiO]_y[O_\frac{1}{2}R'']_z$ wherein Me is a methyl group, R" is an alkyl group having from 5 to 18 carbon atoms inclusive in which the R" groups represent from 15 to 70 weight percent of the alkoxysiloxane.

8. The high resilience polyurethane foam produced by the process as defined in claim 7.

9. A composition consisting essentially of a minor amount of an alkoxysilicon composition selected from the group consisting of:
(1) an alkoxysilane monomer having the average formula,

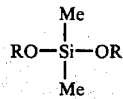

wherein Me is a methyl group and R is an alkyl group having from 6 to 18 carbon atoms inclusive;
(II) an alkoxysiloxane copolymer having the average formula,

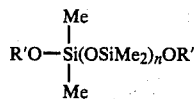

where Me is a methyl group, R' is an alkyl group having from 7 to 18 carbon atoms inclusive in which the R' groups represent from 15 to 75 weight percent of the alkoxysiloxane copolymer, and n has an average value from one to 12 inclusive; and
(III) an alkoxysiloxane copolymer having the average formula,

$[MeSiO_{3/2}]_x[Me_2SiO]_y[O_\frac{1}{2}R'']_z$ wherein Me is a methyl group, R" is an alkyl group having from 5 to 18 carbon atoms inclusive in which the R" groups represent from 15 to 70 weight percent of the alkoxysiloxane copolymer, x has an average value from one to 3 inclusive, y has an average value from zero to (18-x) inclusive, and z has an average value from 3 to 5 inclusive; and a major amount of a solvent therefor, said solvent being selected from the group consisting of polyether triols, polyether diols and polyether monools, trimethylolpropane, 1,2,6-hexanetriol, ethylene glycol, butanol, and or nonylphenol starters.

10. A composition as claimed in claim 9 wherein the alkoxysilicon composition is present in the amount of from one to 20 weight percent and the solvent is present in the amount of from 80 to 99 weight percent.

11. A process for producing high resilience polyurethane foam having a density no greater than 2.0 pounds per cubic foot which comprises simultaneously reacting and foaming a reaction mixture containing: (a) an organic polyol selected from the group consisting of (i) a polyether triol containing at least 40 mole percent primary hydroxyl groups and having a molecular weight from about 2,000 to about 8,000 and (ii) a mixture of said polyether triol and other polyethers having an average of at least two hydroxyl groups, said polyether triol of said mixture amounting to at least 40 weight percent of the total polyol content; (b) a polyisocyanate said organic polyol and said polyisocyanate being present in the mixture in a major amount and in a relative amount required to produce the polyurethane foam; (c) a blowing agent in a minor amount sufficient to foam the reaction mixture; (d) a catalytic amount of catalysts for the production of polyurethane foam; and (e) a foam stabilizer consisting essentially of an alkoxysilicon composition and a solvent as defined in claim 17.

12. The high resilience polyurethane foam produced by the process as defined in claim 11.

13. A process as defined in claim 1 wherein R, R' and R" have an molecular weight greater than 150.

14. A process as defined in claim 1 wherein R" is pentyl.

15. A process as defined in claim 1 wherein R and R" are hexyl.

16. A process as defined in claim 1 wherein R' is 2-ethyl hexyl.

17. A process as defined in claim 1 wherein R, R' and R" are heptyl.

18. A process as defined in claim 1 wherein R, R' and R" are octyl.

19. A process as defined in claim 1 wherein R is nonyl.

20. A process as defined in claim 1 wherein R is decyl.

21. A process as defined in claim 1 wherein R is undecyl.

22. A process as defined in claim 1 wherein R is dodecyl.

23. A process as defined in claim 1 wherein R is tridecyl.

24. A process as defined in claim 1 wherein R is tetradecyl.

25. A process as defined in claim 1 wherein R is pentadecyl.

26. A process as defined in claim 1 wherein R is hexadecyl.

27. A foam as claimed in claim 2 wherein the foam has a density no greater than 1.75 pounds per cubic foot.

28. A foam as claimed in claim 2 wherein the foam has a density no greater than 1.05 pounds per cubic foot.

29. A foam as claimed in claim 4 wherein the foam has a density no greater than 1.75 pounds per cubic foot.

30. A foam as claimed in claim 4 wherein the foam has a density no greater than 1.05 pounds per cubic foot.

31. A foam as claimed in claim 6 wherein the foam has a density no greater than 1.75 pounds per cubic foot 32. A foam as claimed in claim 6 wherein the foam has a density no greater than 1.05 pounds per cubic foot.

33. A foam as claimed in claim 8 wherein the foam has a density no greater than 1.75 pounds per cubic foot.

34. A foam as claimed in claim 8 wherein the foam has a density no greater than 1.05 pounds per cubic foot.

35. A foam as claimed in claim 12 wherein the foam has a density no greater than 1.75 pounds per cubic foot.

36. A foam as claimed in claim 12 wherein the form has a density no greater than 1.05 pounds per cubic foot.

* * * * *

UNITED STATES PATENT AND TRADEMARK OFFICE
CERTIFICATE OF CORRECTION

PATENT NO. : 4,306,035
DATED : December 15, 1981
INVENTOR(S) : Baskent et al

It is certified that error appears in the above—identified patent and that said Letters Patent is hereby corrected as shown below:

On the Title Page

Under Attorney, Agent or Firm, please delete "Faxio" and insert therefor --FAZIO--.

In the Specification

Column 29, Table D, Example XXIX, please delete "$[MeSiO_{3/2}][Me_2SiO]_6[O_{178}(CH_2)_5CH_3]_3$" and insert therefor-- $[MeSiO_{3/2}][Me_2SiO]_6[O_{1/2}(CH_2)_5CH_3]_3$--.

In the Claims

Column 37, Claim 7, line 28, after "alkoxysiloxane" please add --copolymer, x has an average value from one to 3 inclusive, y has an average value from zero to (18-x) inclusive and z has an average value from 3 to 5 inclusive--.

Signed and Sealed this

Fifteenth Day of June 1982

[SEAL]

Attest:

GERALD J. MOSSINGHOFF

Attesting Officer  Commissioner of Patents and Trademarks